(12) United States Patent
Lichtenstein et al.

(10) Patent No.: US 10,196,670 B2
(45) Date of Patent: Feb. 5, 2019

(54) METHODS AND KITS FOR MEASURING PROTEASE ACTIVITY IN FEED

(71) Applicant: Novus International Inc., St. Charles, MO (US)

(72) Inventors: Drew L. Lichtenstein, St. Charles, MO (US); Amie Lawhorn, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 4 days.

(21) Appl. No.: 15/180,850

(22) Filed: Jun. 13, 2016

(65) Prior Publication Data

US 2016/0369320 A1    Dec. 22, 2016

Related U.S. Application Data

(60) Provisional application No. 62/182,065, filed on Jun. 19, 2015.

(51) Int. Cl.
*C12Q 1/37* (2006.01)

(52) U.S. Cl.
CPC .............. *C12Q 1/37* (2013.01); *C12Y 304/00* (2013.01); *C12Q 2337/12* (2013.01); *G01N 2333/956* (2013.01)

(58) Field of Classification Search
CPC .................................................. C12Q 2337/12
See application file for complete search history.

(56) References Cited

U.S. PATENT DOCUMENTS

| 7,629,139 | B2 | 12/2009 | Basu et al. |
| 2006/0286621 | A1 | 12/2006 | Basu et al. |
| 2014/0255965 | A1 | 9/2014 | Wang et al. |

FOREIGN PATENT DOCUMENTS

| WO | WO2001058276 | * | 8/2001 | ............. A23K 1/165 |
| WO | WO2014/164687 | * | 10/2014 | ............. A23K 1/165 |

OTHER PUBLICATIONS

Pedersen et al. J. Anim. Sci., 2012, 90:350-352.*
Novozymes, May 2014, pp. 1-4.*
Stark et al., "Evaluation of Keratinase stability in pelleted broiler diets." Journal of Applied Poultry Research 18:30-33. 2009.

* cited by examiner

*Primary Examiner* — Bin Shen
(74) *Attorney, Agent, or Firm* — Polsinelli PC

(57) ABSTRACT

Methods for measuring protease activity in feed and kits comprising components for measuring protease activity in feed.

10 Claims, 13 Drawing Sheets
(13 of 13 Drawing Sheet(s) Filed in Color)
Specification includes a Sequence Listing.

METHODS AND KITS FOR MEASURING PROTEASE ACTIVITY IN FEED

CROSS-REFERENCE TO RELATED APPLICATIONS

This application claims the priority of U.S. Provisional Application Ser. No. 62/182,065, filed Jun. 19, 2015, the content of which is hereby incorporated by reference in its entirety.

FIELD OF THE INVENTION

The invention describes methods and kits for measuring protease activity in feed.

BACKGROUND OF THE INVENTION

Proteases are used as animal feed additives to improve livestock health and performance, yet few methods for quantifying protease activity in animal feed have been published. Moreover, those methods often involve special equipment, complicated procedures, or specialized knowledge, which make such analyses very difficult to perform at the locations where the results are most useful. In some cases, a qualitative result may be sufficient to determine if the protease was added to the feed at the correct dosage, or if a sufficient amount of enzyme withstood feed production conditions such as pelleting.

Although there are many protease assays known, none of them addresses all of the obstacles inherent in trying to quantify the activity of an exogenously added protease in the context of animal feed. The added protease may adsorb to components of the feed, making it difficult to extract the enzyme. An in-feed method for protease activity must address the presence of specific protease inhibitors present in certain feedstuffs. A highly sensitive assay must be used to detect protease activity in feed due to its typically low inclusion level. Endogenous protein substrate in the feed can mask the presence of protease activity and make it difficult to establish appropriate conditions to accurately quantify the added protease. The capacity of animal feed to act as a good buffer means that careful attention must be paid to adjusting the pH since all enzymes function optimally only within a certain range of pH values. Due to these obstacles to conducting in-feed assays for protease activity, existing methods usually require additional steps, which increase assay complexity and decrease accuracy and precision.

Consequently, painstaking efforts and technical expertise are required to transfer these in-feed methods to the locations where they would be most useful (i.e., feed mills). Alternatively, shipping samples to a central laboratory for analysis incurs additional cost and time, and the feed has often been used before the results are obtained.

Therefore, there is a need for simple, calibrated methods to detect protease activity in feed that can be performed on-site and without the need for sophisticated equipment.

SUMMARY

Among the various aspects of the present disclosure is the provision of a method for measuring protease activity in a feed sample. The method comprises preparing a reaction mixture by combining the feed sample, a protease substrate, and a reaction buffer comprising phosphate, wherein the protease substrate comprises a polypeptide attached to a signal producing group which generates a signal upon proteolytic cleavage of the protease substrate. The method further comprises incubating the reaction mixture under conditions that allow for cleavage of the protease substrate such that the signal is generated, and measuring protease activity in the reaction mixture by measuring the signal.

Another aspect of the disclosure encompasses a kit for measuring protease activity in a feed sample. The kit comprises a protease substrate comprising a polypeptide attached to a signal producing group that generates a signal upon proteolytic cleavage of the polypeptide, and a reaction buffer comprising phosphate. In some embodiments, the kit further comprises an extraction buffer.

Other aspects and features of the disclosure are detailed below.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION

Figure 1A:
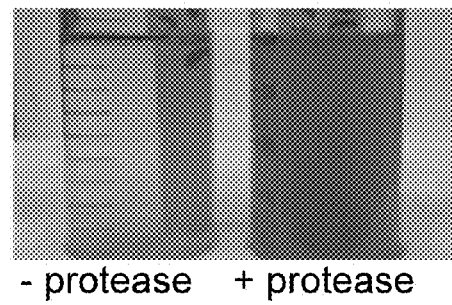
FIG. 1A shows images of protease activity assays in which solutions of keratin azure protease substrate were incubated in the absence or presence of protease.

Provided herein are methods and kits for detecting or measuring protease activity in feed. Advantageously, the methods are straight-forward, accurate, and do not require the use of expensive equipment such as pH measuring devices and centrifugation or filtration devices. Additionally, it has been discovered that phosphate buffer can be used in methods of measuring protease activity in feed. As such, the methods of the present invention can be performed at the site of feed/food processing without the use of expensive equipment, and obviating the need to ship the samples off-site for analysis and, thus, avoiding lengthy delays in obtaining results.

I. Methods

Provided herein are methods for detecting and/or measuring protease activity in feed. The methods may be used for qualitative or quantitative measurement of protease activity in feed samples. Generally speaking, qualitative measurement is used to determine the presence (or absence) of a protease in a feed sample. Alternatively, quantitative measurement is used to determine the amount of protease activity in a feed sample. The methods generally comprise (a) preparing a reaction mixture by combining a feed sample, a substrate for a protease, and a reaction buffer comprising phosphate, and (b) incubating the reaction mixture under conditions that allow for cleavage of the polypeptide such that the signal is produced for measurement of the protease activity.

(a) Preparing a Reaction Mixture

The method for measuring protease activity involves forming a reaction mixture. A reaction mixture typically comprises a feed sample, a substrate for a protease, and a reaction buffer that typically comprises phosphate. In some iterations of the invention involving quantitative measurement, the method further comprises preparing a protease extract from the feed sample before preparing the reaction mixture. Each component of the reaction mixture is described below.

i. Feed Sample

The reaction mixture of the method disclosed herein includes a feed sample. The terms "feed", "food", "feed sample", and "food sample", are herein used interchangeably and may refer to any sample containing a protease activity to be measured. The feed sample may include one or more components of an animal feed. Non-limiting examples of feed matter or animal feed matter may include, without limitation: corn or a component of corn, such as, for example, corn meal, corn fiber, corn hulls, corn DDGS (distiller's dried grain with solubles), silage, ground corn, corn germ, corn gluten, corn oil, or any other portion of a corn plant; soy or a component of soy, such as, for example, soy oil, soy meal, soy hulls, soy silage, ground soy, or any other portion of a soy plant; wheat or any component of wheat, such as, for example, wheat meal, wheat fiber, wheat hulls, wheat chaff, ground wheat, wheat germ, or any other portion of a wheat plant; canola or any other portion of a canola plant, such as, for example, canola oil, canola meal, canola protein, canola hulls, ground canola, or any other portion of a canola plant; sunflower or a component of a sunflower plant; sorghum or a component of a sorghum plant; sugar beet or a component of a sugar beet plant; cane sugar or a component of a sugarcane plant; barley or a component of a barley plant; palm oil, palm kernel or a component of a palm plant; glycerol; corn steep liquor; a waste stream from an agricultural processing facility; lecithin; rumen protected fats; molasses; soy molasses; flax; peanuts; peas; oats; grasses, such as orchard grass and fescue; fish meal, meat & bone meal; feather meal; and poultry byproduct meal; and alfalfa and/or clover used for silage or hay, and various combinations of any of the feed ingredients set forth herein, or other feed ingredients generally known in the art. As it will be recognized in the art, a feed composition may further be supplemented with amino acids, vitamins, minerals, and other feed additives such as other types of enzymes, organic acids, essential oils, probiotics, prebiotics, antioxidants, pigments, anti-caking agents, and the like.

The feed sample may be formulated for administration to any animal subject. Suitable subjects include humans, food animals, companion animals, research animals, and zoo animals. Non-limiting examples of food animals include poultry (e.g., chickens, including broilers, layers, and breeders, ducks, game hens, geese, guinea fowl/hens, quail, and turkeys), beef cattle, dairy cattle, veal, pigs, goats, sheep, bison, and fishes. Suitable companion animals include, but are not limited to, cats, dogs, horses, rabbits, rodents (e.g., mice, rats, hamsters, gerbils, and guinea pigs), hedgehogs, and ferrets. Examples of research animals include rodents, cats, dogs, rabbits, pigs, and non-human primates. Non-limiting examples of suitable zoo animals include non-human primates, lions, tigers, bears, elephants, giraffes, and the like.

According to various embodiments of the present invention, the feed sample may be in any suitable form known in the animal feed art, and may be a wet or dry component. For example, according to certain embodiments, the feed composition may be in a form selected from the group consisting of a complete feed, a feed supplement, a feed additive, a premix, a top-dress, a tub, a mineral, a meal, a block, a pellet, a mash, a liquid supplement, a drench, a bolus, a treat, and combinations of any thereof. Additionally, a feed sample may optionally be ground before preparing a reaction mixture.

The feed sample may include a protease as an animal feed additive. Proteases are used in the agricultural industry for a variety of purposes, such as, e.g., to improve the digestibility of the feed. Proteases used as animal feed additives are generally known in the art. Suitable proteases include endoproteases and exoproteases. In various embodiments, the protease may be an aspartic protease, an asparagine protease, a cysteine protease, a glutamic protease, a metalloprotease, a serine protease, a threonine protease, a protease of unknown catalytic mechanism, or combinations thereof. In one preferred embodiment, the protease may be a heat stable protease from *Bacillus*. In another preferred embodiment, the protease may be a serine protease from *Bacillus*. In yet another preferred embodiment, the protease may be a broad spectrum protease from *Bacillus*. In a further preferred embodiment, the protease may be a protease from *Bacillus licheniformis*. The strain of *B. licheniformis* may be PWD-1.

The amount of protease(s) that may be added to animal feed can and will vary. In general, the amount of protease(s) added to animal feed may range from about 10 azocasein units of protease activity in one gram of feed (U/g) to about 1000 U/g. For instance, the amount of protease(s) added to animal feed may be about 10, 50, 100, 150, 200, 250, 300, 350, 400, 450, 500, 550, 600, 650, 700, 750, 800, 850, 900, 950, or about 1000 U/g. In some embodiments, the amount of protease(s) added to animal feed may be about 100, 110, 120, 130, 140, 50, 60, 70, 80, 90, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or about 500 U/g. In preferred embodiments, the amount of protease(s) added to animal feed may be about 200, 210, 220, 230, 240, 250, 260, 270, 280, 290, 300, 310, 320, 330, 340, 350, 360, 370, 380, 390, or about 400 U/g.

The amount of the feed sample used to prepare the reaction mixture can and will vary. In general, the amount of the feed sample may be about 1, 5, 10, 15, 20, 25, 30, 35, 40, 45, 50, 55, or about 60 grams or more. In some embodiments, about 1, 2, 3, 4, 5, 6, 7, 8, 9, 10, 11, 12, 13, 14, or about 15 grams of the feed sample is used to prepare the reaction mixture. In preferred embodiments, about 3, 3.5, 4, 4.5, 5, 5.5, 6, 6.5, 7, 7.5, or about 8 grams of feed is used to prepare the reaction mixture. In exemplary embodiments, about 5 grams of feed is used to prepare the reaction mixture.

ii. Protease Substrate

The reaction mixture also comprises a substrate for a protease. A suitable substrate generally includes a polypeptide attached to a signal producing group such that the signal is produced upon cleavage of the polypeptide by a protease that is being measured.

The term "polypeptide" is used in its broadest sense and may include peptides, polypeptides, and proteins, as well as peptides, polypeptides, and proteins that contain one or more non-natural amino acids or any other chemical modification that allows the polypeptide to function as a substrate for a protease enzyme whose activity is being measured. The polypeptide may be a naturally occurring polypeptide, such as, e.g., casein, collagen, gelatin, albumin, globin, and the like. Alternatively, the polypeptide may be a synthetic peptide or polypeptide.

Signal producing groups can provide signals detectable by such techniques as colorimetric, fluorescent, electrochemical, spectroscopic, chromatographic, densitometric, or radiographic techniques, and the like. Suitable signal producing groups for the present invention include, but are not limited to, radioactive atoms, fluorescent dyes, chromophores, chemiluminescent labels, electrochemiluminescent labels, ligands having specific binding partners, or any other signal producing groups that can interact with each other to enhance, alter, or diminish a signal. It is also contemplated that signal producing groups may be molecules that do not themselves produce a detectable signal, but when used in conjunction with another label can produce or quench a detectable signal. For example, a label may be a quencher of a quencher-dye pair. For instance, the quencher-dye pair is comprised of a fluorophore and a quencher. A signal producing group of a substrate may be attached to a polypeptide substrate by any means, including by covalent or non-covalent means, such that a signal can be produced by the signal producing group upon cleavage of the polypeptide while present in a feed sample by the protease that is being measured.

In some embodiments, the signal producing group of the protease substrate may be a fluorophore. Suitable fluorophores include, but are not limited to, fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), and near infrared (NIR) (700-900 nm) fluorescent dyes.

In other embodiments, the signal producing group of the protease substrate may be a radioisotope. Non-limiting examples of suitable radionuclides include technetium-99m, ilodine-123, 125, and 131, thallium-201, gallium-67, fluorine-18, fluorodeoxyglucose, and indium-111.

In other embodiments, the signal producing group of the protease substrate may be a chromophore. A chromophore produces a signal comprising a visible change in color if a substrate is cleaved. Non-limiting examples of suitable chromophores include Erioglaucine, Reactive Black 5, Reactive Blue 21, Reactive Orange 78, Reactive Yellow 15, Reactive Blue 19, Reactive Blue 4, Reactive Red 11, Reactive Yellow 86, Reactive Blue 163, Reactive Red 180, mono- and dihalogentriazine dyes such as mono- and di-fluorotriazine dyes, mono- and di-chlorotriazine dyes, mono-(m'-carboxypyridinium) triazines, dyes in the PROCION® line of dyes, the CIBACRON™ line of coal tar colors, 2,4,5 trihalogenopyriminidines, 2,3 dihaloquinoxalines, N-hydroxysulfosuccinimidyl (sulfo-NHS) ester functionalized dyes, N-hydroxysuccinimidyl (NHS) functionalized dyes, vinyl sulfone dyes such as the REMAZOL® line of coal tar dyestuffs including REMAZOL® Blue, azo dyes such as Sudan I, Sudan II, Sudan III, Sudan IV, Sudan Black, Disperse Orange, Disperse Red, Oil Red O, Trypan Blue, Congo Red, β-carotene, p-nitroanilide (pNA), sulfonyl chloride dyes such as lissamine, rhodamine, and dabsyl chloride, tetrafluorophenyl ester functionalized dyes, isothiocyanate functionalized dyes, and iodoacetyl functionalized dyes and other dyes that are structurally equivalent to the dyes listed herein.

The protease substrate may be insoluble. As used herein, the term "insoluble" refers to a substrate that is incapable of dissolving in an aqueous phosphate buffer at a pH from about 6 to about 9 and at a temperature of about 25° C. to about 50° C. As such, a substrate that is insoluble is generally non-homogeneously distributed, physically separate, and visually distinguishable from the bulk of the reaction buffer. Non-limiting examples of insoluble substrates suitable for use in methods of the present invention include hide-Remazol Brilliant Blue R, azo collagen, Azurine cross-linked casein, gelatin-Remazol Brilliant Blue, casein-Remazol Brilliant Blue, and collagen-Remazol Brilliant Blue. In an exemplary embodiment, an insoluble substrate is casein-Remazol Brilliant Blue.

Alternatively, the protease substrate may be soluble. As used herein, the term "soluble" refers to a substrate that is capable of dissolving in an aqueous phosphate buffer at a pH from about 6 to about 9 and at a temperature of about 25° C. to about 50° C. to form a homogeneous solution. Non-limiting examples of suitable soluble substrates include N-succinyl-Ala-Ala-Pro-Phe(SEQ ID NO:1)-p-nitroanilide, N-succinyl-Ala-Ala-Pro-Leu(SEQ ID NO:2)-p-nitroanilide, N-succinyl-Ala-Ala-Pro-Arg(SEQ ID NO:3)-p-nitroanilide, N-methylsulfonyl-D-Phe-Gly-Arg-p-nitroanilide, and o-aminobenzoyl-AGSRGAGQ(SEQ ID NO:4)-(2,3-dinitrophenyl-ethylene diamine). In a preferred embodiment, a soluble substrate is N-succinyl-Ala-Ala-Pro-Leu(SEQ ID NO:2)-p-nitroanilide. In an exemplary embodiment, a soluble substrate is N-succinyl-Ala-Ala-Pro-Phe(SEQ ID NO:2)-p-nitroanilide.

iii. Reaction Buffer

The reaction mixture also comprises a reaction buffer. In preferred embodiments, a reaction buffer comprises phosphate. By way of non-limiting example, a reaction buffer may comprise TRIS (tris(hydroxymethyl)aminomethane), TRIS HCl, 3-{[tris(hydroxymethyl)methyl]amino}propanesulfonic acid (TAPS), N,N-bis(2-hydroxyethyl)glycine (Bicine), tris(hydroxymethyl)methylamine (tris), N-tris(hydroxymethyl)methylglycine (tricine), 3-[N-Tris(hydroxymethyl)methylamino]-2-hydroxypropanesulfonic acid (TAPSO), 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (cacodylate), saline sodium citrate (SSC), 2-(N-morpholino)ethanesulfonic acid (MES), 2(R)-2-(methylamino)succinic acid (succinic acid), borate, phosphate, acetate, glycine, magnesium or calcium carbonate, and bicarbonate. In exemplary embodiments, the reaction buffer comprises sodium phosphate or potassium phosphate.

The pH of a reaction buffer can and will vary. For example, the reaction buffer may be adjusted to a pH of about 6.0 to about 12.0. For instance, the reaction buffer may be adjusted to a pH of about 6.0, 6.5, 7.0, 7.5, 8.0, 8.5, 9.0, 9.5, 10.0, 10.5, 11.0, 11.5, or about 12.0. In some embodiments, the reaction buffer has a pH of about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or about 9.0. In other embodiments, the reaction buffer has a pH of about 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or about 10.0. In yet other embodiments, the reaction buffer has a pH of about 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9 or about 11.0. In a preferred embodiment, the reaction buffer has a pH of about 7.5, 7.6, 7.7, 7.8, 7.9, 8.0, 8.1, 8.2, 8.3, 8.4, or about 8.5. In another preferred embodiment, the reaction buffer has a pH of about 8.5, 8.6, 8.7, 8.8, 8.9, 9.0, 9.1, 9.2, 9.3, 9.4, or about 9.5. In yet another preferred embodiment, the reaction buffer has a pH of about 9.5, 9.6, 9.7, 9.8, 9.9, 10.0, 10.1, 10.2, 10.3, 10.4, or about 10.5. In an exemplary embodiment, the reaction buffer has a pH of about 8.0. In another exemplary embodiment, the reaction buffer has a pH of about 10.0.

The concentration of the buffering agent in the reaction buffer is typically sufficient to maintain a desired pH range and as a result, can and will vary. The concentration of the buffering agent in the reaction buffer for example may be about 20, 30, 40, 50, 60, 70, 80, 90, 100, 110, 120, 130, 140, 150, 160, 170, 180, 190, or about 200 mM. In some embodiments, the concentration of the buffering agent in the reaction buffer is about 50, 60, 70, 80, 90, 100, 110, 120, 130, 140, or about 150 mM. In preferred embodiments, the concentration of the buffering agent in the reaction buffer is about 50, 55, 60, 65, 70, 75, 80, 85, 90, 95, 100, 105, 110, 115, 120, 125, 130, 135, 140, 145, or about 150 mM. In more preferred embodiments, the concentration of the buffering agent in the reaction buffer is about 90, 91, 92, 93, 94, 95, 96, 97, 98, 99, 100, 101, 102, 103, 104, 105, 106, 107, 108, 109, or about 110 mM. In an exemplary embodiment, the concentration of phosphate buffer in the reaction buffer is about 100 mM.

The reaction buffer may optionally include a denaturing agent. Denaturing agents suitable for use in the present invention may be any agent capable of disrupting secondary and tertiary structures of a polypeptide and are known in the art. Non-limiting examples of denaturing agents that may be used in the reaction buffer include solvents such as ethanol and methanol; cross-linking agents such as formaldehyde and glutaraldehyde; chaotropic agents; and surface acting agents such as cetyltrimethylammonium bromide (CTAB), 3-[(3-cholamidopropyl)dimethylammonio]-1-propanesulfonate (CHAPS), sodium laureth sulfate (sodium dodecyl sulfate or SDS), polyoxyethylene (10) cetyl ether (BRIJ® 56), polyoxyethylene (20) cetyl ether (BRIJ® 58), polyoxyethyleneglycol dodecyl ether (BRIJ® 35), polyoxyethylene (9) p-t-octyl phenol (NONIDET™ P-40), polyoxyethylene (4-5) p-t-octyl phenol (TRITON™ X-45), polyoxyethylene (7-8) p-t-octyl phenol (TRITON™ X-114), polyoxyethylene (9-10) p-t-octyl phenol (TRITON™ X-100), polyoxyethylene (9-10) nonylphenol (TRITON™ N-101), a polysorbate surface active agent such as polyoxyethylene (20) sorbitol monolaurate (TWEEN® 20), polyoxyethylene (20) sorbitol monopalmitate (TWEEN® 40), Polyoxyethylene (20) sorbitan monostearate (Tween® 60), and polyoxyethylene (20) sorbitol monooleate (TWEEN® 80).

In some embodiments, the denaturing agent may be a chaotropic agent. Non-limiting examples of chaotropic reagents suitable for use in the method may be urea, guanidinium chloride, lithium perchlorate, 2-mercaptoethanol, dithiothreitol, and TCEP (tris(2-carboxyethyl)phosphine). In an alternative of the embodiments, the chaotropic denaturing agent may be guanidinium chloride. In another alternative, the chaotropic denaturing agent may be lithium perchlorate. In a preferred embodiment, the chaotropic denaturing agent may be urea. As will be appreciated by a skilled artisan, a denaturing concentration of urea may range from about 5M to about 8M. In an exemplary alternative of the embodiments, the concentration of urea in the reaction buffer of the method disclosed herein is about 6M urea.

In other embodiments, the denaturing agent may be a surface acting agent. In some embodiments, the surface acting denaturing agent may be a non-ionic surface acting agent. A preferred non-ionic surface active agent may be a polysorbate surface active agent such as Tween® 20, Tween® 40, Tween® 60, or Tween® 80. In alternative embodiments, the surface acting denaturing agent may be an anionic surface acting agent. In some embodiments, the surface acting agent may be SDS. The weight fraction of SDS in the reaction buffer may be in the range of from about 0.001% to about 20%. In some alternatives of the embodiments, the weight fraction of SDS in the reaction buffer may be in the range of from about 0.1% to about 10%. In other alternatives of the embodiments, the weight fraction of SDS in the reaction buffer may be in the range of about 1% to about 4%. In exemplary embodiments, the weight fraction of SDS in the reaction buffer used in the methods disclosed herein is about 0.25%.

In embodiments in which protease activity is measured quantitatively, the buffer may be 100 mM sodium phosphate, and have a pH of about 10.0. In other embodiments in which protease activity is measured qualitatively, the buffer may be 100 mM sodium phosphate, 6M urea, and have a pH of about 8.0. In certain embodiments in which protease activity is measured qualitatively, the buffer may be 100 mM sodium phosphate, 0.25% SDS, and have a pH of about 8.0.

The reaction buffers may further comprise salts such as sodium chloride (NaCl) or potassium chloride (KCl), reducing agents such as dithiothreitol (DTT), β-mercaptoethanol (BME), and tris(2-carboxyethyl)phosphine (TCEP), bulking agents such as dextran sulfate, polyethylene glycol (PEG), an anti-foaming agent to prevent excessive foaming or frothing, enzymatic inhibitors, and tetraethylene glycol, and others.

iv. Mixing the Components

The order of addition of the various components of a reaction mixture can and will vary depending on the feed sample, the protease to be detected or measured, and the protease substrate. In some embodiments, a reaction mixture may be prepared by adding the reaction buffer to the protease substrate and the feed sample in a test tube. In other embodiments, a reaction mixture may be prepared by adding the reaction buffer to the feed sample in a test tube and adding the protease substrate to the mixture of reaction buffer and feed sample. In some preferred embodiments, a reaction mixture may be prepared by adding the protease substrate and the feed sample to the reaction buffer in a test tube. In other preferred embodiments, a reaction mixture may be prepared by adding the reaction buffer to the protease substrate in a test tube and adding the feed sample to the mixture of reaction buffer and protease substrate. The amount of various components of a reaction mixture can and will vary, and may be determined experimentally.

v. Preparing Feed Extracts or Protease Extracts

In some embodiments, a feed extract is prepared by mixing the feed sample with the reaction buffer and allowing the feed sample to settle in the feed extract. In general, the feed sample is not ground prior to being mixed with the reaction buffer. An aliquot of the feed extract (which comprises the reaction buffer) is then mixed with the protease substrate to form the reaction mixture. The feed extract may be filtered prior to being mixed with the protease substrate to form the reaction mixture.

In other embodiments in which the signal is measured quantitatively, the method may further comprise preparing a protease extract of the feed sample before preparing the reaction mixture. In general, the protease extract is prepared by (a) grinding a feed sample, (b) mixing the ground feed with an extraction buffer, and (c) clarifying the mixture of ground feed and extraction buffer to generate the protease extract.

Methods of grinding a feed sample are known in the art. In preferred embodiments, a feed sample is ground using a Fritsch rotor speed mill. A feed sample may be ground to a particle size of about 10, 9, 8, 7, 6, 5, 4, 3, 2, 1, 0.5, or about 0.1 mm or less. In preferred embodiments, a feed sample is ground to a particle size of about 10, 9, 8, 7, 6, 5, 4, 3, 2, or about 1 mm or less. In exemplary embodiments, a feed sample is ground to a particle size of about 1 mm or less.

Suitable extraction buffers are known in the art. In preferred embodiments, the extraction buffer may be an aqueous borate buffer. For example, the extraction buffer may comprise sodium borate, sodium tetraborate, or potassium borate.

The pH of the extraction buffer may range from about 7.0 to about 13.0. For instance, the extraction buffer may have a pH of about 7.0, 7.5, 8.0, 8.5, 9.0, 9.5, 10.0, 10.5, 11.0, 11.5, 12.0, 12.5, or about 13.0. In some embodiments, the extraction buffer may have a pH of about 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9 or about 11.0. In a preferred embodiment, the extraction buffer may have a pH of about 9.5, 9.6, 9.7, 9.8, 9.9, 10.0, 10.1, 10.2, 10.3, 10.4, or about 10.5. In an exemplary embodiment, the extraction buffer has a pH of about 10.0.

The concentration of the borate in the extraction buffer may be about 20, 30, 40, 50, 60, 70, 80, 90, 100, 110, 120, 130, 140, 150, 160, 170, 180, 190, or about 200 mM. In some embodiments, the concentration of the borate in the extraction buffer is about 50, 60, 70, 80, 90, 100, 110, 120, 130, 140, or about 150 mM. In preferred embodiments, the concentration of the borate in the extraction buffer is about 50, 55, 60, 65, 70, 75, 80, 85, 90, 95, 100, 105, 110, 115, 120, 125, 130, 135, 140, 145, or about 150 mM. In more preferred embodiments, the concentration of the borate in the extraction buffer is about 90, 91, 92, 93, 94, 95, 96, 97, 98, 99, 100, 101, 102, 103, 104, 105, 106, 107, 108, 109, or about 110 mM. In an exemplary embodiment, the concentration of borate in the extraction buffer is about 100 mM.

The extraction buffer may optionally further include a denaturing agent. Suitable denaturing agents for use in an extraction buffer are known in the art. In one preferred embodiment, the denaturing agent may be a nonionic surfactant, such as, e.g., polyoxyethylene (20) sorbitol monolaurate (TWEEN® 20) or polyoxyethylene (9-10) p-t-octyl phenol (TRITON™ X-100). The amount of nonionic surfactant in the extraction buffer may be about 0.1, about 0.2, about 0.3, about 0.4, about 0.5, about 0.6, about 0.7, about 0.8, about 0.9, or about 1.0% by weight.

The duration of mixing the feed sample with the extraction buffer can and will vary depending on the type of feed sample, the concentration of protease in the feed sample, and the temperature at which the extraction is conducted, and can be determined experimentally. In general, the feed sample may be mixed with the extraction buffer for about 1, 5, 10, 20, 30, 40, 50, or about 60 min. In some embodiments, the feed sample is mixed with the extraction buffer for about 1, 2, 3, 4, 5, 6, 7, 8, 9, 10, 11, 12, 13, 14, 15, 16, 17, 18, 19, or about 20 min. In preferred embodiments, the feed sample is mixed with the extraction buffer for about 10 min.

The protease extract may be clarified before being mixed with the other components to from the reaction mixture. Methods of clarifying an extract are known in the art. For instance, the protease extract may be clarified by centrifugation or filtration. In preferred embodiments, the protease extract is clarified by centrifugation before being mixed with the other components.

Lastly, the reaction mixture is prepared by combining the protease extract with the reaction buffer and the protease substrate. In some embodiments, the reaction buffer comprises phosphate. For example, the reaction buffer may comprise from about 50 mM to about 200 mM phosphate at about pH 7 to pH 11. In exemplary embodiments, the reaction buffer comprises about 100 mM sodium or potassium phosphate at about pH 10.

(b) Incubating the Reaction Mixture

Once the reaction mixture is prepared as detailed in section (I)(a) above, the methods disclosed herein typically involve incubating the reaction mixture under conditions that allow for cleavage of the protease substrate. As will be appreciated by a skilled artisan, the conditions and time required for incubation of the reaction mixture can and will vary depending on the feed sample, the concentration of protease in the feed sample, and the identity of the protease substrate used in preparing a reaction mixture. In general, the reaction mixture may be incubated at a temperature ranging from about ambient temperature to about 100° C. For instance, the reaction mixture may be incubated at a temperature of about 15, 20, 25, 30, 35, 40, 45, 50, 55, 60, 65, 70, 75, 80, 85, 90, 95, or about 100° C. Typically, the reaction mixture is incubated until a sufficient amount of signal is developed to allow for determination of protease activity. For instance, the duration of incubation may range from about 1 minute to about 10 hours or more.

(c) Measuring Protease Activity

The next step of the method comprises measuring protease activity in the reaction mixture. The method of measurement can and will vary. Protease activity is generally determined by measuring a signal produced upon cleavage of the protease substrate by the protease in the reaction mixture. In preferred embodiments, the signal producing group is a chromophore. When a signal producing group is a chromophore, the signal may be measured qualitatively through visual inspection of a color change resulting from the signal produced by the chromophore. Alternatively, when the signal producing group is a chromophore, the signal may be measured quantitatively through spectrophotometric detection of the signal generated by the chromophore.

i. Qualitative Measurement

In some embodiments, protease activity is measured qualitatively. As used herein, the term "qualitative" refers to the simple determination of the presence or absence of protease in the feed sample. As such, a method of the present invention may be used to determine if a protease has been added to the4 feed sample and/or if the protease activity has survived the feed preparation process. Generally, when protease activity is measured qualitatively, protease activity is measured through visual inspection of a color change resulting from the signal produced by the chromophore.

In preferred alternatives of the embodiments, the signal producing group is a chromophore, and the measuring is qualitative through visual inspection of a color change resulting from the signal produced by the chromophore. In exemplary alternatives of the embodiments, the substrate is insoluble, the signal producing group is a chromophore, and the measuring is through visual inspection of a color change resulting from the signal produced by the chromophore.

When protease activity is measured qualitatively, the method disclosed herein may further be optimized to determine the presence or absence of a minimum amount of protease activity in a feed sample. A minimum amount of protease activity in a feed sample may be about 50 U/g feed to about 500 U/g feed. For instance, a minimum amount of protease activity in a feed sample may be about 50, 60, 70, 80, 90, 100, 150, 160, 170, 180, 190, 200, 300, 400, or about 500 U/g feed. In some embodiments, a minimum amount of protease activity in a feed sample is about 50, 60, 70, 80, 90, 100, 110, 120, 130, 140, or about 150 U/g feed. In other embodiments, a minimum amount of protease activity in a feed sample is about 100, 110, 120, 130, 140, 150, 160, 170, 180, 190, or about 200 U/g feed. In yet other embodiments, a minimum amount of protease activity in a feed sample is about 150, 160, 170, 180, 190, 200, 210, 220, 230, 240, or about 250 U/g feed. In additional other embodiments, a minimum amount of protease activity in a feed sample is about 200, 210, 220, 230, 240, 250, 260, 270, 280, 290, or about 300 U/g feed. In other embodiments, a minimum amount of protease activity in a feed sample is about 250, 260, 270, 280, 290, 300, 310, 320, 330, 340, or about 350 U/g feed. In yet other embodiments, a minimum amount of protease activity in a feed sample is about 300, 310, 320, 330, 340, 350, 360, 370, 380, 390, or about 400 U/g feed. In additional embodiments, a minimum amount of protease activity in a feed sample is about 350, 360, 370, 380, 390, 400, 410, 420, 430, 440, or about 450 U/g feed. In other embodiments, a minimum amount of protease activity in a feed sample is about 400, 410, 420, 430, 440, 450, 460, 470, 480, 490, or about 500 U/g feed. In preferred embodiments, a minimum amount of protease activity in a feed sample is about 130, 135, 140, 145, 150, 155, 160, 165, 170, 175, 180, 185, 190, 195, or about 200 U/g feed. In exemplary embodiment, a minimum amount of protease activity in a feed sample is about 150 U/g feed.

A method may be optimized by adjusting the reaction buffer composition, including the buffering agent, the buffering agent concentration, the buffer pH, the presence or absence of a denaturant, the identity of the denaturant, the concentration of denaturant, and combinations thereof. Alternatively, a method may be optimized by adjusting the reaction conditions, including the reaction time, the reaction temperature, and the amount of feed included in the reaction mixture. In a preferred embodiment, a method is optimized by adjusting the concentration of denaturant in the reaction buffer. In exemplary embodiments, the denaturant is SDS, and the concentration of SDS in a reaction buffer is about 0.25%.

ii. Quantitative Measurement

In some embodiments, protease activity is measured quantitatively. As used herein, the term "quantitative" may refer to the accurate determination of the amount of protease activity in a feed sample. For instance, a method of the present invention may be used to determine the absolute amount of protease activity present in a feed or how much of the protease activity has survived the feed preparation process.

Generally, when protease activity is measured quantitatively, protease activity is measured through spectrophotometric measurement of a signal produced. In preferred alternatives of the embodiments, the signal producing group is a chromophore, and the measuring is quantitative through spectrophotometric measurement of a signal produced. In exemplary alternatives of the embodiments, the substrate is soluble and the signal producing group is a chromophore, and wherein the measuring is quantitative through spectrophotometric measurement of a signal produced.

When protease activity is measured quantitatively, the method disclosed herein are suitable for determining protease activity over a wide range of protease concentrations. For instance, the method may be suitable for determining protease activity in the range of about 1 U/g feed to about 1500 U/g feed or more. In preferred embodiments, the method may be is suitable for determining protease activity in the range of about 40 U/g feed to about 200 U/g feed. In exemplary embodiments, the method may be suitable for determining protease activity in the range of about 40 U/g feed to about 80 U/g mash feed. In other exemplary embodiments, the method may be suitable for determining protease activity in the range of about 100 U/g feed to about 150 U/g pellet feed.

II. Kits

In another aspect, the invention encompasses kits for measuring protease activity in feed. A kit of the present invention may be used to measure protease activity qualitatively or quantitatively by measurement of the amount of a signal produced from a substrate by the activity of a protease in the feed. Methods of measuring protease activity using a kit of the present invention may be as described in section (I) above.

In general, a kit comprises protease substrate as described above in section (I)(a)(ii) and a reaction buffer as detailed above in section (I)(a)(iii). In general, the protease substrate may be dry (i.e., powder, granules, tablets, etc.) and the reaction buffer may be dry (i.e., comprise the components in dry form). In some embodiments, the kit may further comprise an extraction buffer as described above in section (I)(a)(v). The extraction buffer may be provided as a mixture of dry components.

In some embodiments, the kit may be used to measure protease activity qualitatively. In preferred alternatives of the embodiment, a kit may comprise a first tube comprising dry components of a reaction buffer comprising phosphate, a second tube comprising dry protease substrate, wherein the substrate comprises a polypeptide attached to a signal producing group such that the signal is produced upon cleavage of the polypeptide by the protease, and instructions for using the kit to measure the protease activity in the feed.

In some embodiments, the kit may be used to measure protease activity qualitatively. In preferred alternatives of the embodiment, a kit may comprise an extraction buffer for extracting the protease from the feed, a protease substrate for the protease activity to be measured, wherein the protease substrate is a peptide attached to a signal producing group such that the signal is produced upon cleavage of the peptide by the protease, a reaction buffer comprising phosphate, and instructions for using the kit to measure the protease activity in the feed.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds, products and methods without departing from the scope of the invention, it is intended that all matter contained in the above description and in the examples given below, shall be interpreted as illustrative and not in a limiting sense.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present invention, appreciate that many changes can be made in the specific embodiments which are disclosed and still obtain a like or similar result without departing from the spirit and scope of the invention.

Example 1. Identifying Protease Substrates Suitable for a Protease Assay

The following experiments were performed to develop a protease assay for measuring protease activity in feed. In this example, different materials were first tested for their suitability as a protease substrate. The substrate materials included azure dye-impregnated sheep's wool keratin (i.e., keratin azure), ground animal hides conjugated to Remazol Brilliant Blue R dye (i.e., hide-Remazol), and azo dye impregnated collagen (i.e., azo collagen).

Figure 1B:
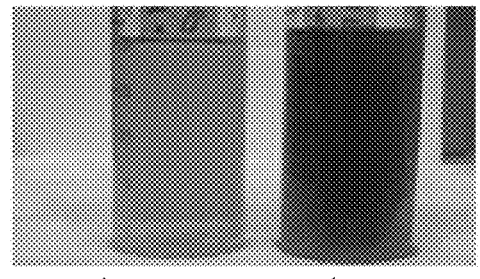
FIG. 1B presents images of protease activity assays in which solutions of hide-Remazol Brilliant Blue R protease substrate were incubated in the absence or presence of protease.
Figure 1C:
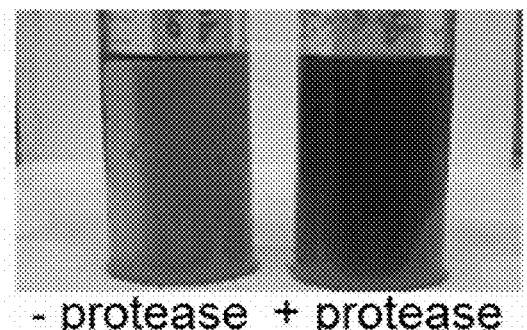
FIG. 1C shows images of protease activity assays in which solutions of azo collagen protease substrate were incubated in the absence or presence of protease.

The materials were incubated in the presence of a protease-containing product (CIBENZA® DP100, Novus International, Inc.) in 40 ml 100 mM Tris buffer, pH 8.0, at 37° C. for 1 hour, and color development was observed when compared to materials incubated in the same buffer without protease. The protease-containing product used in this experiment was CIBENZA® DP100 (Novus International, Inc.), a feed additive comprising an intrinsically heat stable, potent protease enzyme that optimizes the digestibility of proteins in animal feed ingredients. There was a substantial change in color when hide-Remazol and azo collagen were used as substrates (FIGS. 1B, 1C). The color change with keratin azure was far less pronounced (FIG. 1A). This experiment demonstrates that keratin azure, hide-Remazol Brilliant Blue R, and azo collagen are suitable substrates for assaying proteases normally added to feed.

Example 2. Protease Assay Performed with Protease Added to Feed

The assay detailed in Example 1 was performed in the absence of any feed. In this Example, the protease assay was performed in feed extracts with or without added protease. The protease was added to the feed at a concentration of 0.025% and 0.05% (w/w) of feed. About 10 g of feed with or without added protease was extracted with 40 ml 100 mM Tris pH 8.0, and filtered through 0.45 μm PVDF filter before incubating the extract in the presence of protease substrate at 50° C. The protease substrates used included Protazyme AK tablets (Megazyme International) or hide-Remazol Brilliant Blue R. The Protazyme tablets comprise Azurine-crosslinked casein that hydrate rapidly in water but remain insoluble. Cleavage by the protease releases the soluble dyed polypeptide fragments. All un-reacted substrate settles while the released dyed polypeptide fragments turn the solution blue.

Figure 2A:
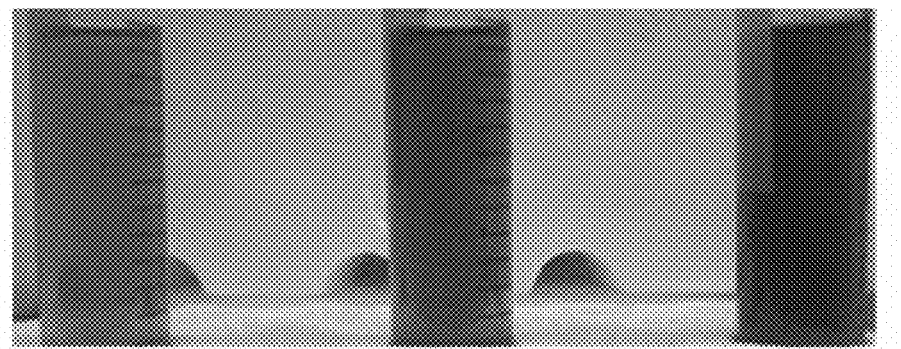
FIG. 2A depicts images of protease activity assays in which solutions comprising feed extract and Protazyme AK protease substrate were incubated in the absence or present of 0.025% or 0.05% protease.
Figure 2B:
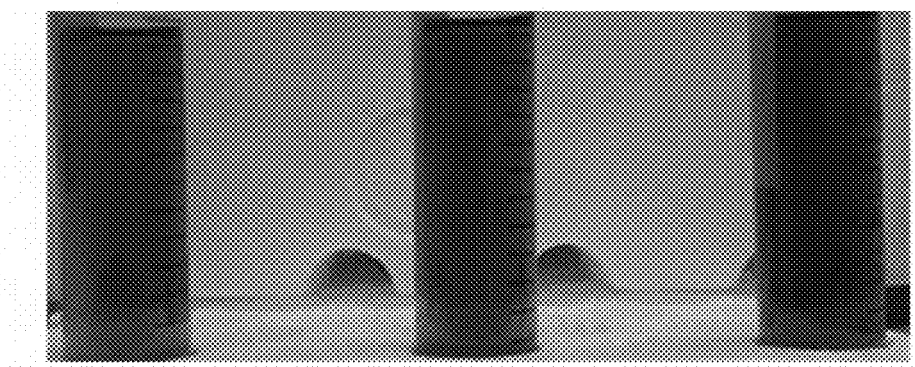
FIG. 2B presents images of protease activity assays in which solutions comprising feed extract and hide-Remazol Brilliant Blue R protease substrate were incubated in the absence or present of 0.025% or 0.05% protease.
Figure 3A:
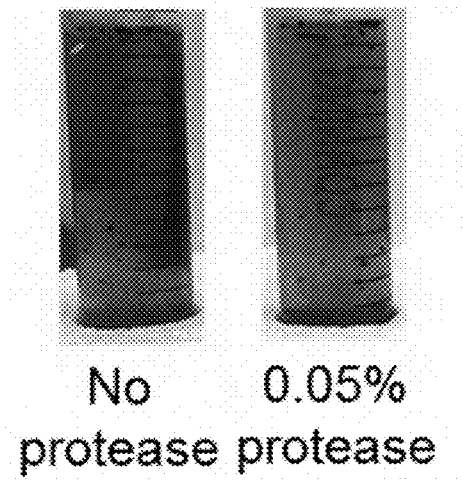
FIG. 3A shows images of protease activity assays in which solutions comprising feed extract and Protazyme AK protease substrate were incubated for 1 hour in the absence or presence of protease.
Figure 3B:
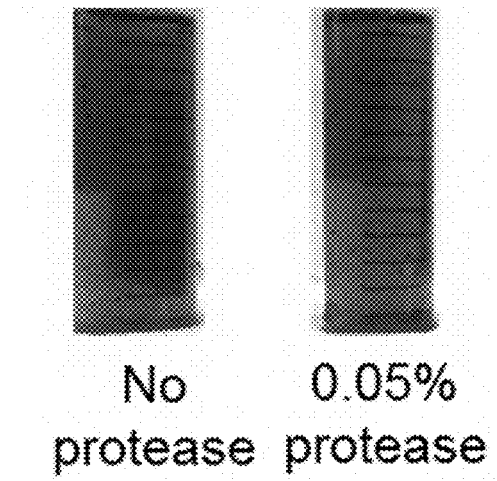
FIG. 3B shows images of protease activity assays in which solutions comprising feed extract and Protazyme AK protease substrate were incubated for 2 hours in the absence or presence of protease.
Figure 3C:
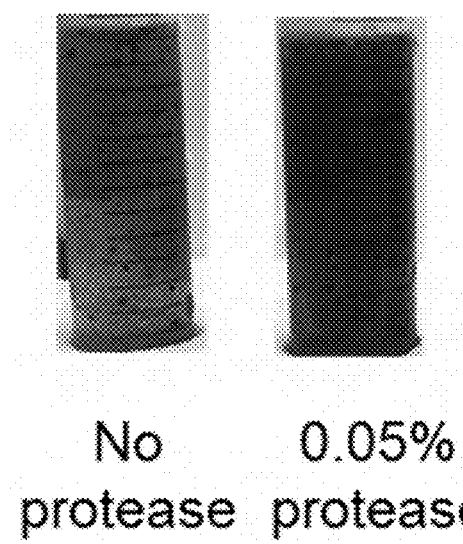
FIG. 3C presents images of protease activity assays in which solutions comprising feed extract, Protazyme AK protease substrate, and 6 M urea were incubated for 1 hour in the absence or presence of protease.
Figure 3D:
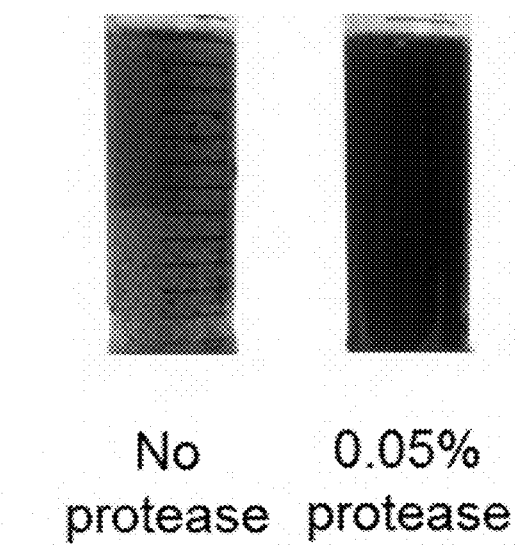
FIG. 3D shows images of protease activity assays in which solutions comprising feed extract, Protazyme AK protease substrate, and 6 M urea were incubated for 2 hours in the absence or presence of protease.
Figure 4A:
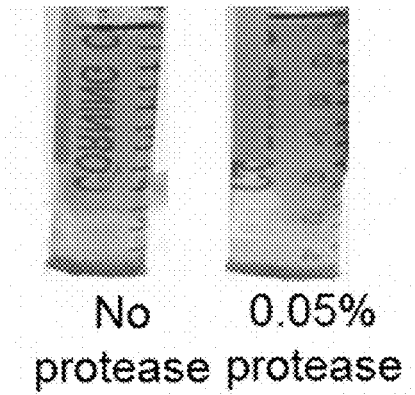
FIG. 4A shows images of protease activity assays in which solutions comprising feed extract and hide-Remazol Brilliant Blue R protease substrate were incubated for 1 hour in the absence or presence of protease.
Figure 4B:
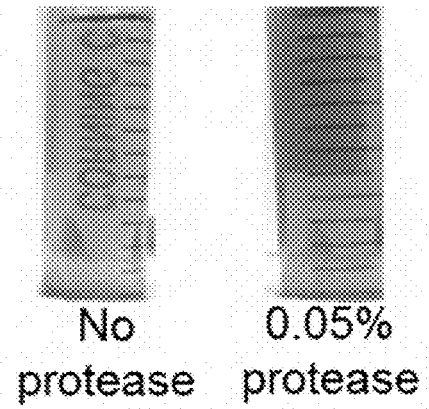
FIG. 4B shows images of protease activity assays in which solutions comprising feed extract and hide-Remazol Brilliant Blue R protease substrate were incubated for 2 hours in the absence or presence of protease.
Figure 4C:
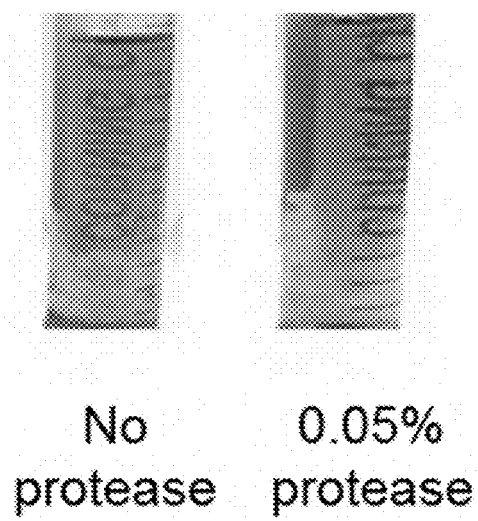
FIG. 4C presents images of protease activity assays in which solutions comprising feed extract, hide-Remazol Brilliant Blue R protease substrate, and 6 M urea were incubated for 1 hour in the absence or presence of protease.
Figure 4D:
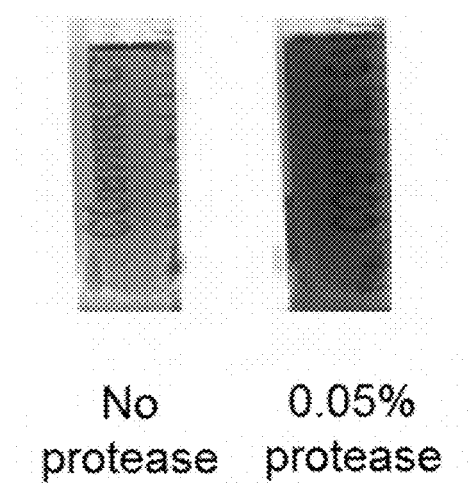
FIG. 4D shows images of protease activity assays in which solutions comprising feed extract, hide-Remazol Brilliant Blue R protease substrate, and 6 M urea were incubated for 2 hours in the absence or presence of protease.

Under these conditions, there was a discernable difference in color development between feed extracts with and without added protease (FIGS. 2A, 2B). Additionally, the color development was concentration-dependent; there was a discernable difference in color development between feed extracts with 0.025% protease and feed extract with 0.05% protease (w/w). However, the difference was only obvious to the naked eye after 5 hours of incubation. There was a substantial color development when either Protazyme AK tablets (FIG. 2A) or hide-Remazol Brilliant Blue R (FIG. 2B) was used. The blue of the hide-Remazol was more discernable than the blue derived from the Protazyme tablets, but the background was also much darker. An additional experiment was performed in which the hide-Remazol was washed prior to using in the qualitative in-feed assay. The background in the control feed (no CIBENZA® DP100) was much lighter than with the unwashed hide-Remazol, allowing the feed containing and lacking CIBENZA® DP100 to be clearly distinguished from each other (data not shown).

Example 3. Urea Accelerates Color Development in Protease Assay

While the reaction conditions used in Example 2 were able to distinguish between feed with and without added protease, it took 5 hours for the difference to become obvious to the naked eye. In the current example, the protease assay was performed with feed with added urea.

In short, about 5 g of feed with or without added protease was extracted with 40 ml 100 mM Tris pH 9.0, and filtered through 0.45 μm PVDF filter before performing the assay. When used, the concentration of urea was 6M. The assay was performed at 50° C., with mixing every 20 min. The protease substrates included Protazyme AK tablets or hide-Remazol Brilliant Blue R. Denaturants such as urea and sodium dodecyl sulfate (SDS) are typically used to unfold proteins, including enzymes, and thereby abolish their function. Unexpectedly, when urea was added to the assay buffer, protein digestion and hence color development in the solution phase of the reaction was accelerated such that feed with protease could be distinguished from feed without added protease in as little as 1-2 hours (FIGS. 3A-D, FIGS. 4A-D).

Example 4. SDS Accelerates Color Development in Protease Assay

Reactions containing 6 M urea, such as the reaction conditions used in Example 3, are difficult to filter. Therefore, an alternative denaturant having the same protease reaction accelerating effect was sought. The denaturant SDS was also tested for its capacity to accelerate the protease reaction. In this example, SDS was tested alone or in combination with urea.

Figure 5A:
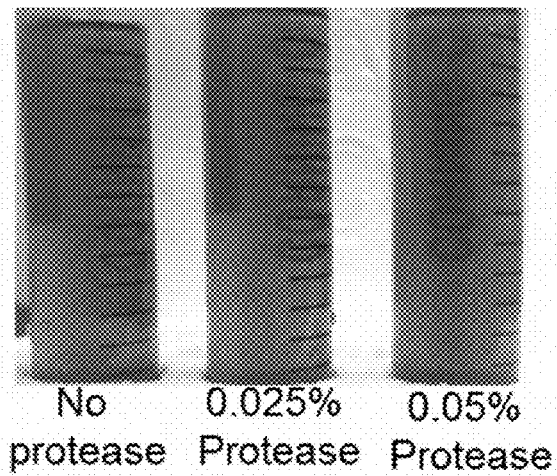
FIG. 5A shows images of protease activity assays in which solutions comprising feed extract and Protazyme AK protease substrate were incubated in the absence or presence of protease.
Figure 5B:
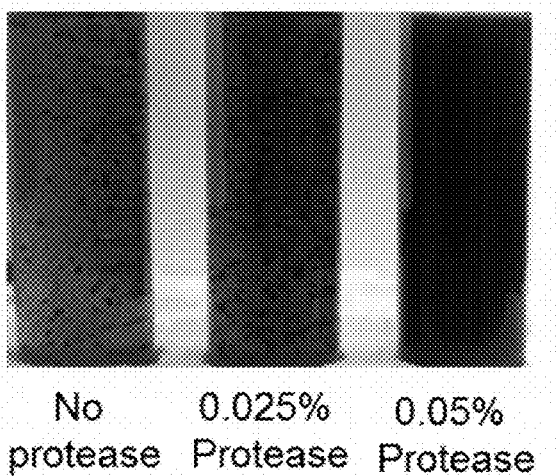
FIG. 5B shows images of protease activity assays in which solutions comprising feed extract, Protazyme AK protease substrate, and 6 M urea were incubated in the absence or presence of protease.
Figure 5C:
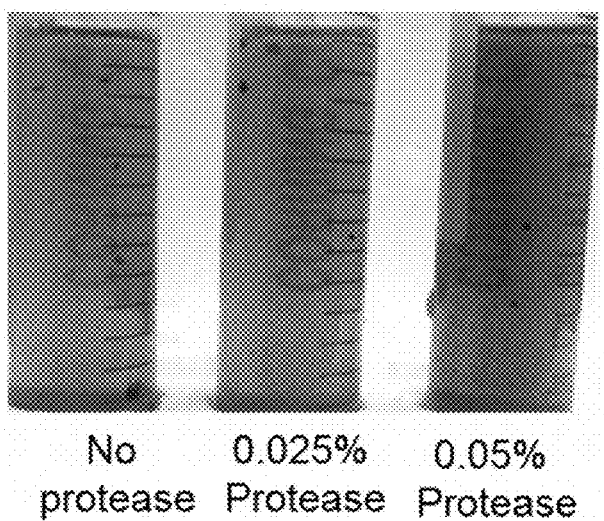
FIG. 5C presents images of protease activity assays in which solutions comprising feed extract, Protazyme AK protease substrate, and 0.05% SDS were incubated in the absence or presence of protease.
Figure 5D:
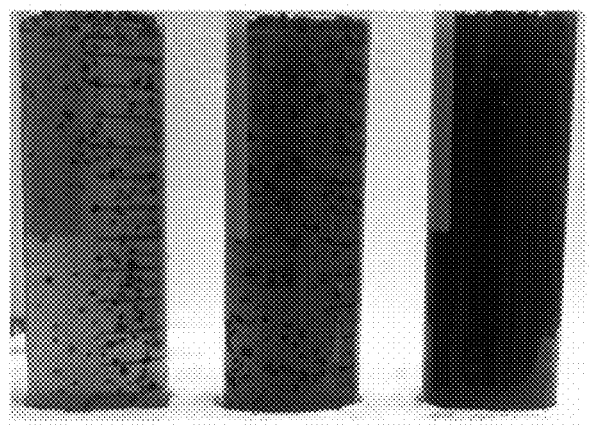
FIG. 5D shows images of protease activity assays in which solutions comprising feed extract, Protazyme AK protease substrate, and 0.1% SDS were incubated in the absence or presence of protease.
Figure 5E:
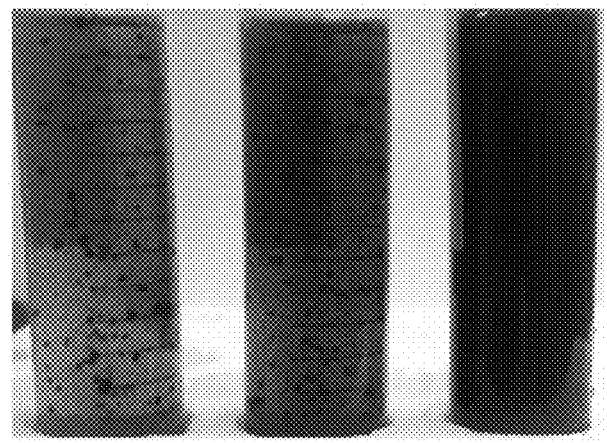
FIG. 5E shows images of protease activity assays in which solutions comprising feed extract, Protazyme AK protease substrate, 0.05% SDS, and 6 M urea were incubated in the absence or presence of protease.

In short, about 5 g of feed with or without added protease was extracted with 40 ml 100 M Tris pH 9.0 and the various denaturants, and filtered through 0.45 μm PVDF filter before performing the assay. The denaturant concentrations were 6M urea, 0.05% SDS, 0.1% SDS, and 0.05% SDS in combination with 6M urea. Protazyme AK was used as the substrate. SDS alone accelerated color development in a concentration-dependent manner such that feed with and without added protease could be distinguished from each other in as little as 2 hours (FIGS. 5C, 5D). After 2 hours of incubation, color development with the combination of 0.05% SDS and 6 M urea (FIG. 5E) was no different than with 6 M urea alone (FIG. 5B). Importantly, 0.1% SDS alone (FIG. 5D) yielded similar results to 6 M urea alone (FIG. 5B) suggesting that SDS might be as good as 6 M urea in accelerating the protease reaction.

Example 5. Protease Assay Performed with Higher Concentrations of SDS

Figure 6A:
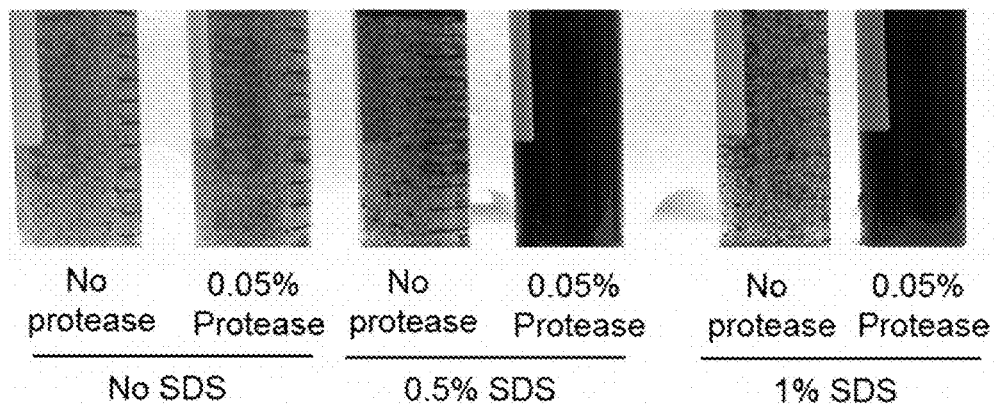
FIG. 6A shows images of protease activity assays without added denaturants, with 0.05% SDS, or with 1% SDS. Shown is protease activity using Protazyme AK protease substrate after 30 minutes incubation.
Figure 6B:
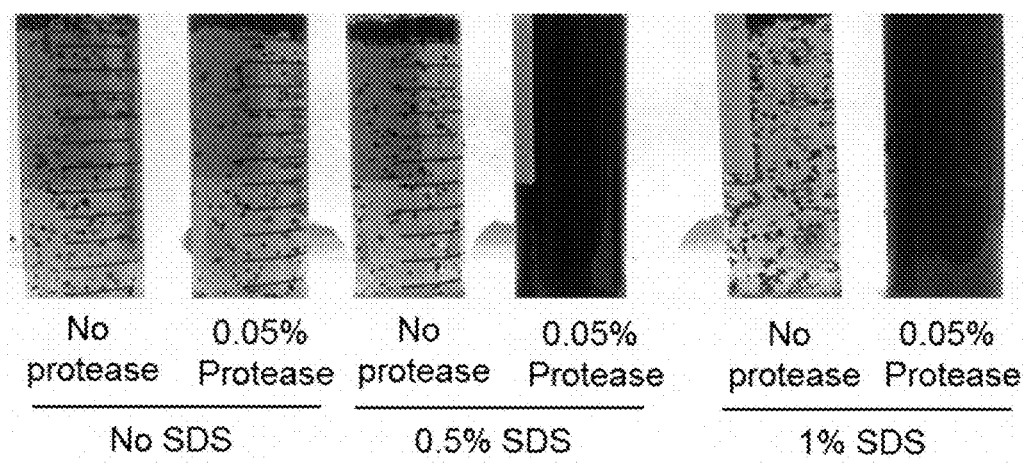
FIG. 6B presents images of protease activity assays without added denaturants, with 0.05% SDS, or with 1% SDS. Shown is protease activity using Protazyme AK protease substrate after 60 minutes incubation.
Figure 6C:
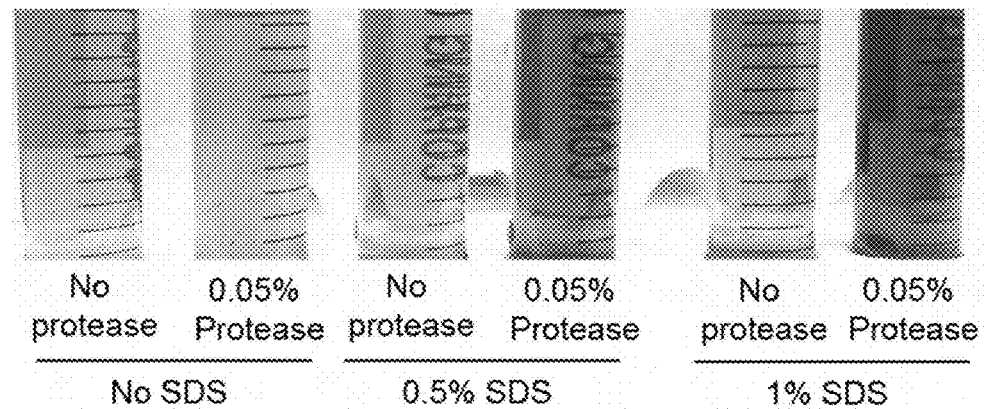
FIG. 6C shows images of protease activity assays without added denaturants, with 0.05% SDS, or with 1% SDS. Presented is protease activity using hide-Remazol Brilliant Blue R protease substrate after 30 minutes incubation.
Figure 6D:
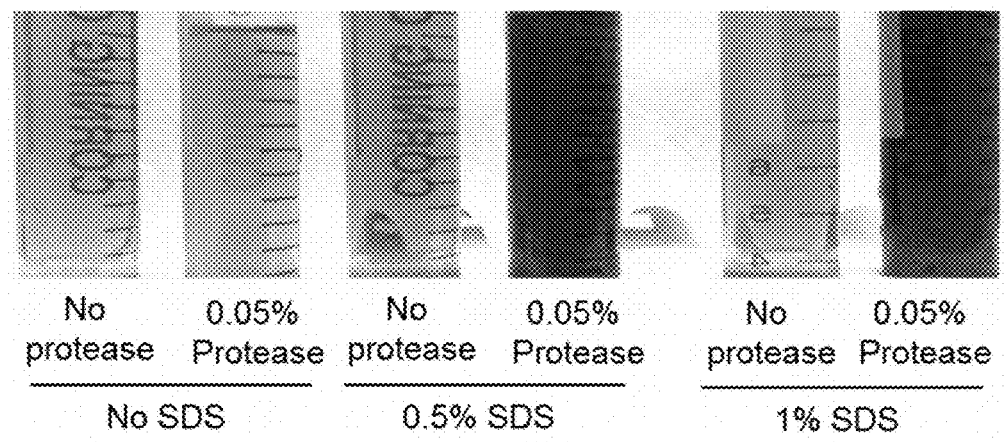
FIG. 6D presents images of protease activity assays without added denaturants, with 0.05% SDS, or with 1% SDS. Shown is protease activity using hide-Remazol Brilliant Blue R protease substrate after 60 minutes incubation.
Figure 7A:
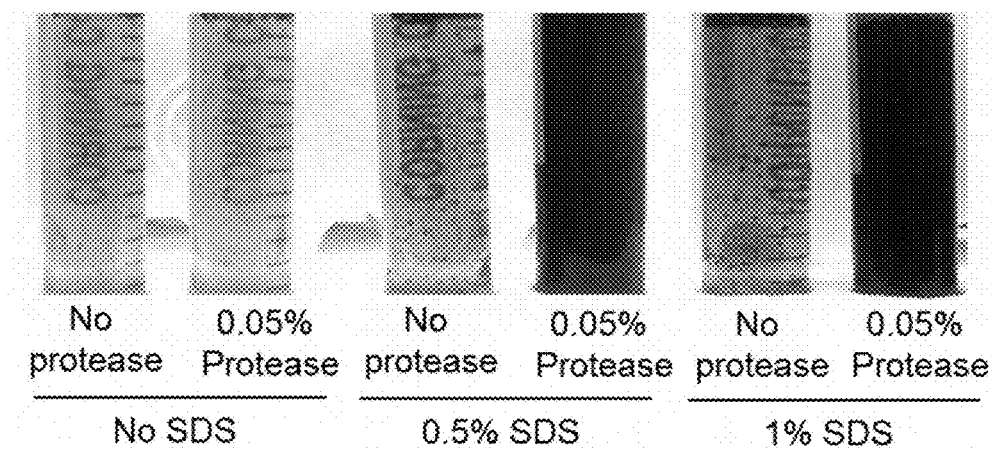
FIG. 7A shows images of protease activity assays in phosphate buffer without added denaturants, with 0.05% SDS, or with 1% SDS. Presented is protease activity assay using Protazyme AK protease substrate after 30 minutes incubation.
Figure 7B:
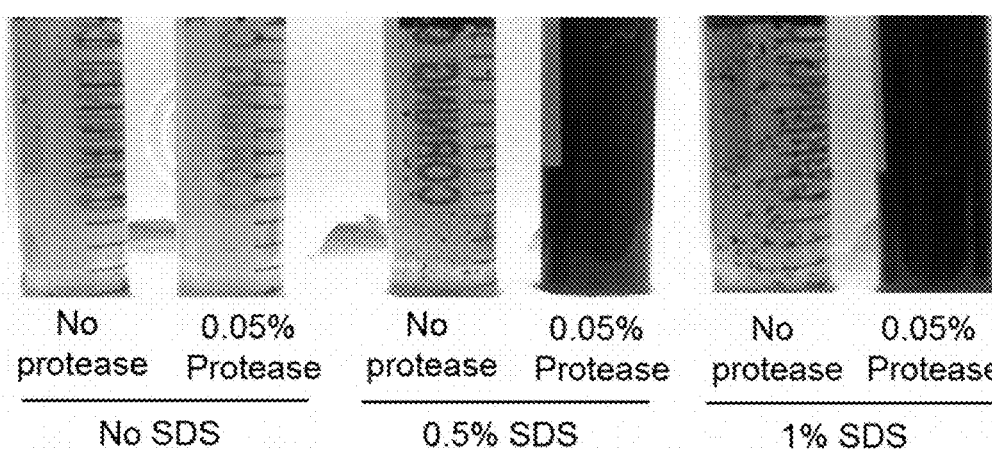
FIG. 7B presents images of protease activity assays in phosphate buffer without added denaturants, with 0.05% SDS, or with 1% SDS. Presented is protease activity assay using Protazyme AK protease substrate after 60 minutes incubation.
Figure 7C:
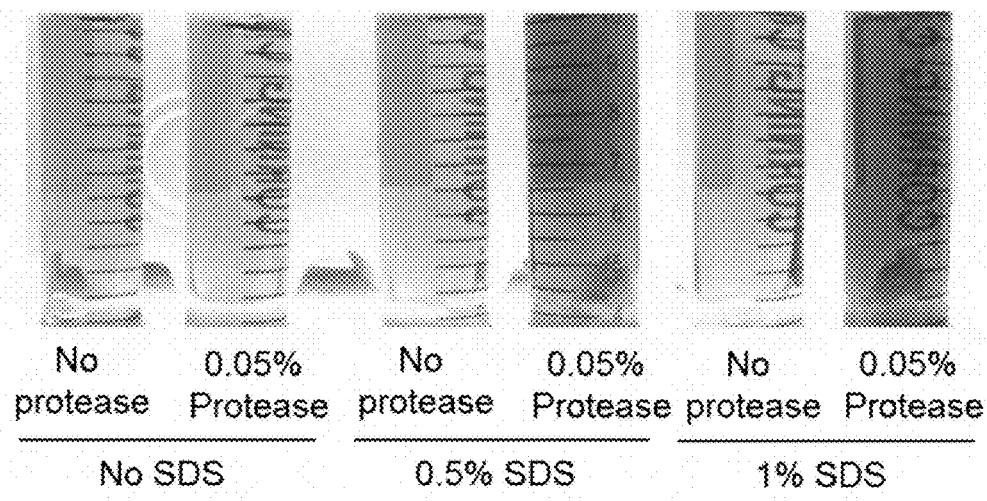
FIG. 7C shows images of protease activity assays in phosphate buffer without added denaturants, with 0.05% SDS, or with 1% SDS. Presented is protease activity assay using hide-Remazol Brilliant Blue R protease substrate after 30 minutes incubation.
Figure 7D:
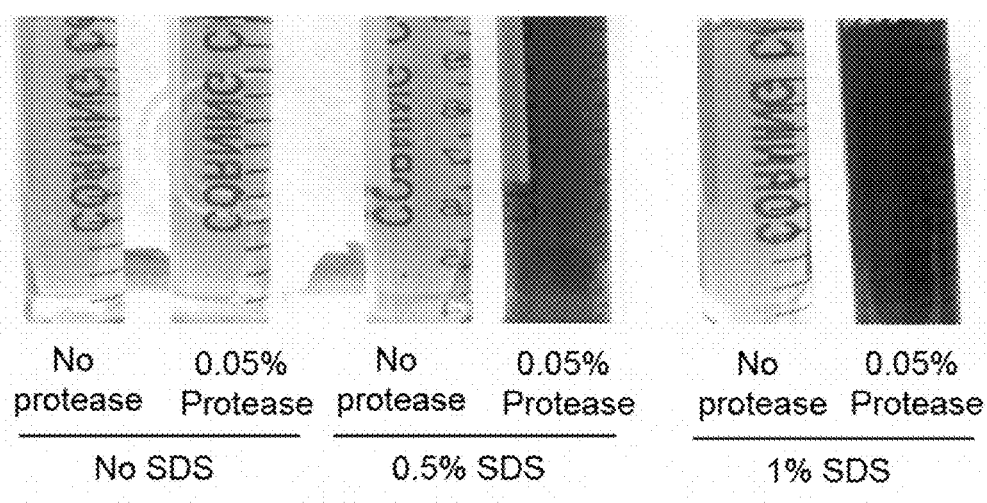
FIG. 7D presents images of protease activity assays in phosphate buffer without added denaturants, with 0.05% SDS, or with 1% SDS. Presented is protease activity assay using hide-Remazol Brilliant Blue R protease substrate after 60 minutes incubation.
Figure 8A:
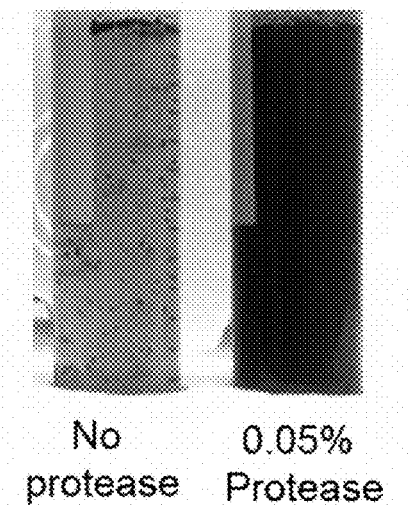
FIG. 8A depicts images of protease activity assays with unfiltered feed extract. Presented is protease activity assay using Protazyme AK protease substrate after 30 minutes incubation.
Figure 8B:
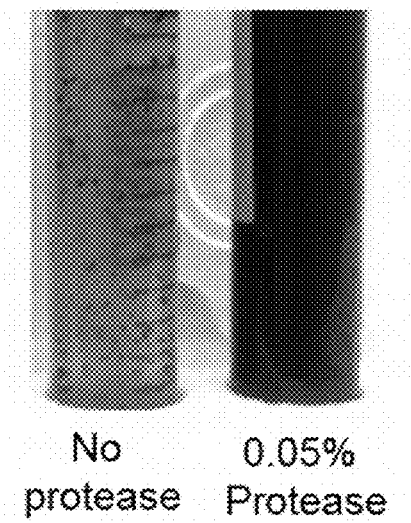
FIG. 8B depicts images of protease activity assays with unfiltered feed extract. Presented is protease activity assay using Protazyme AK protease substrate after 60 minutes incubation.
Figure 8C:
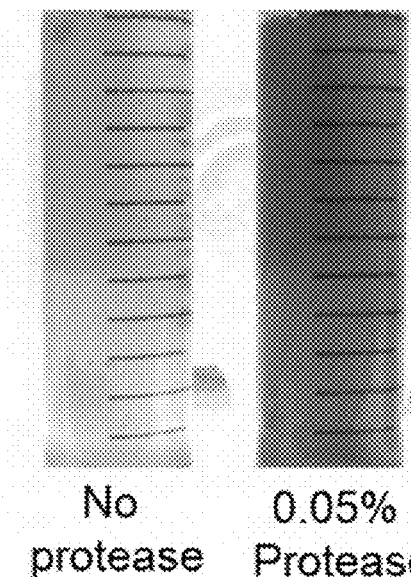
FIG. 8C depicts images of protease activity assays with unfiltered feed extract. Presented is protease activity assay using hide-Remazol Brilliant Blue R protease substrate after 30 minutes incubation.
Figure 8D:
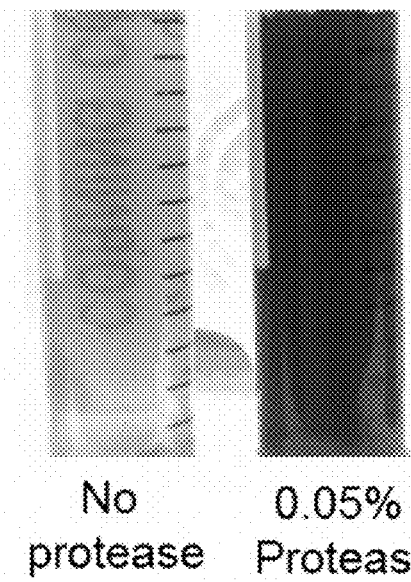
FIG. 8D depicts images of protease activity assays with unfiltered feed extract. Presented is protease activity assay using hide-Remazol Brilliant Blue R protease substrate after 60 minutes incubation.

Based on the concentration-dependent acceleration of the reaction in the presence of SDS seen above, higher concentrations of SDS were tested for their effect on the rate of color development. In this experiment, the SDS concentration was 1%, and the protease substrates were Protazyme AK and hide-Remazol Brilliant Blue R. The reaction was incubated at 50° C. for 30 or 60 minutes. Surprisingly, 0.5% and 1.0% SDS were capable of accelerating the reaction to such an extent that the solution was nearly opaque by 30 minutes when Protazyme AK was used as the substrate (FIGS. 6A, 6B). In addition, the presence of SDS in the buffer clearly accelerated color development when hide-Remazol Brilliant Blue R was used as the substrate (FIGS. 6C, 6D).

Example 6. Phosphate Buffer can be Used in the Protease Assay

Next, the use of phosphate as a buffer instead of Tris was explored to develop an assay that requires as little equipment as possible. By using phosphate as the buffer, a mixture of powdered monobasic sodium phosphate and dibasic sodium phosphate could be supplied to achieve the appropriate pH when hydrated with water, thereby eliminating the need for the end user to prepare the Tris buffer, which would necessitate a pH meter. However, it has been suggested that buffers essentially free of phosphate are needed to observe protease activity in a complex matrix such as animal feed.

About 5 g of feed with or without added protease was extracted with 40 ml 100 mM phosphate buffer pH 8.0 and 0.05% or 1% SDS, and filtered through 0.45 μm PVDF filter before performing the assay. Protazyme AK or hide-Remazol was used as the substrate. The reaction was incubated at 50° C. for 30 or 60 minutes. Unexpectedly, including SDS at either 0.5% or 1.0% when phosphate was used as the buffer, abrogated the need to use a buffer essentially free of phosphate when either Protazyme AK or hide-Remazol Brilliant Blue R were used as a substrate (FIGS. 7A-D).

Example 7. Protease Assay can be Performed with Unfiltered Feed Extract

To simplify the method even further, the possibility of eliminating the need to filter the feed extract was explored. Feed extract was prepared by shaking the feed in 40 ml buffer (100 mM phosphate pH 8.0+1.0% SDS). The large feed particles were then allowed to settle for 20-30 seconds, and a portion (about 8 ml) of the supernatant was then transferred to a fresh tube containing about 2 ml pre-hydrated substrate. Protazyme AK or hide-Remazol was used as the substrate. The reaction was incubated at 50° C. for 30 or 60 minutes. There was a clear difference in color between the unfiltered feed extract lacking or containing protease, indicating that unfiltered feed extract can be used in the method (FIGS. 8A-D).

Example 8. Development of Protease Assay Calibrated to Detect a Minimum Level of Protease in Feed A method calibrated to yield a signal only when a certain minimum level of protease is present would be useful for users to determine if sufficient protease is present in the feed to achieve the desired biological effect. Therefore, conditions of the method were altered such that only a minimum of approximately 150 U/g feed of CIBENZA® DP100 protease activity would be detectable.

In short, about 5 g of feed with or without added protease was extracted with 40 ml 100 mM phosphate buffer pH 8.0 and 0.25% SDS. The protease (CIBENZA® DP100) was added to the feed at concentrations of 0, 75, 150, 225, 300, and 375 U/g feed. Protazyme AK was used as the substrate. The reaction was incubated at 50° C. for 1 hr.

Figure 9:
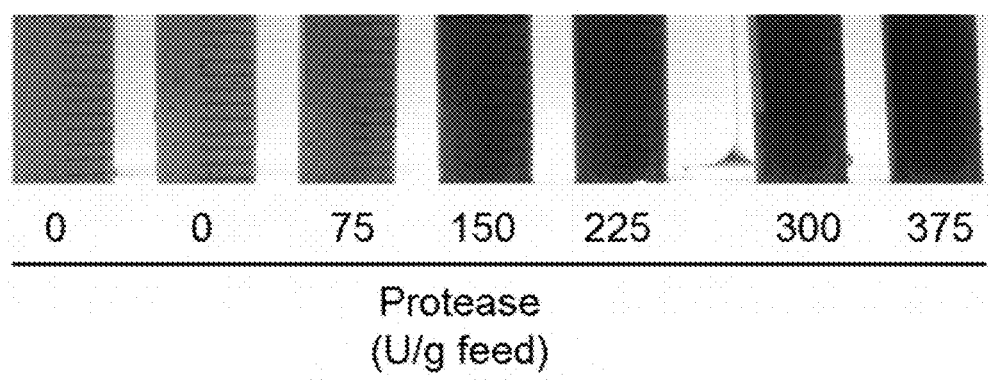
FIG. 9 depicts images showing calibrated measurement of protease activity assay in samples comprising various amounts of protease and using Protazyme AK protease substrate after 60 minutes incubation.

By lowering the SDS concentration to 0.25%, the method was calibrated such that the feed needed to contain at least 150 U/g feed before a discernable signal was observed (FIG. 9).

Example 9. Protease Assay Using Various Feed Sources

Figure 10A:
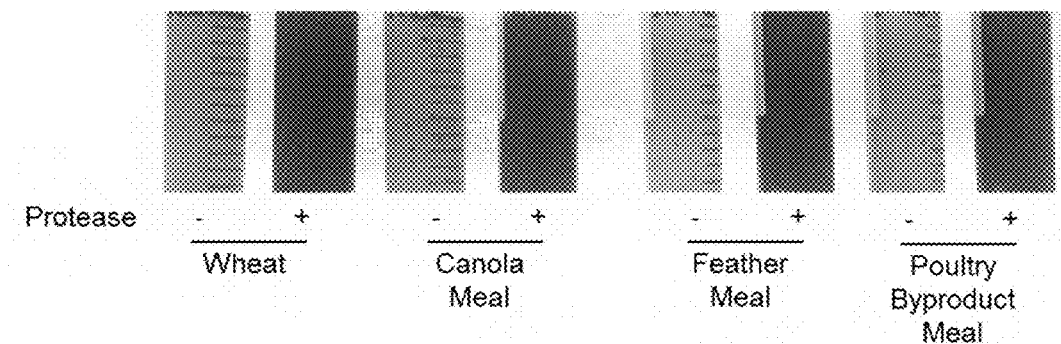
FIG. 10A depicts images showing measurements of protease activity assays using the indicated feed formulations.
Figure 10B:
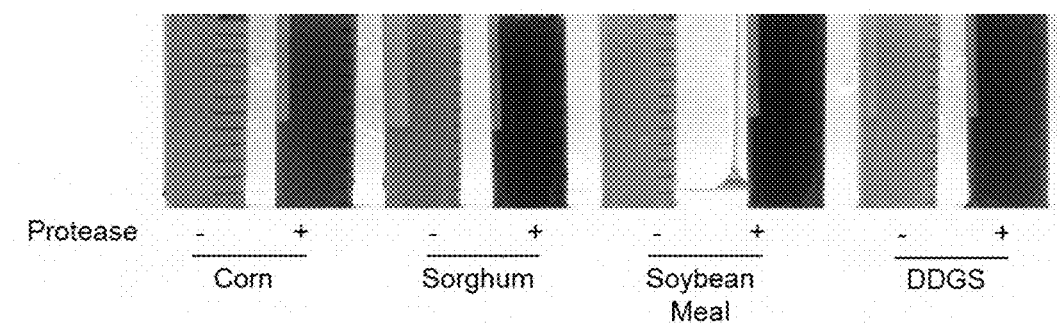
FIG. 10B depicts images showing measurements of protease activity assays using the indicated feed formulations.

Feed formulations within and between world areas differ based on the availability and cost of different feed ingredients. To be useful in different parts of the world, the qualitative detection method must be able to detect protease in the presence of different feed ingredients. To examine the robustness of the method with respect to different ingredients, eight different semi-purified diets containing or lacking a protease product were evaluated using the assay as described in Example 8. Each diet consisted of a single protein source plus starch as a carbohydrate source. Protease activity was detectable in all eight diets showing that all of the tested ingredients were compatible with detecting protease activity by this method (FIGS. 10A, 10B).

Example 10. Quantitative Protease Assay Protocol

It is sometimes of interest to determine the exact amount of active protease in a feed. Therefore, a quantitative method was also developed and then validated. The quantitative method quantifies active protease in feed by spectrophotometric measurement of the chromophore para-nitroaniline (pNA), which is released from the synthetic peptide substrate Succinyl-Ala-Ala-Pro-Phe(SEQ ID NO:1)-p-nitroaniline upon cleavage of the amide bond that links the chromophore to the peptide. The free chromophore is detected by measuring the optical density at 410 nm. The steps of the method consist of (1) preparing the feed by grinding it and then mixing the feed with an extraction buffer consisting of 100 mM sodium tetraborate and Tween® 20 at pH 10.0, (2) preparing a reaction consisting of (a) a reaction buffer comprising sodium phosphate at pH 10, (b) a substrate, and (c) a portion of the feed extract and then incubating at 37° C. to allow the protease in the feed extract to cleave the substrate and (3) stopping the reaction with a solution comprising acetic acid and sodium dodecyl sulfate and then quantifying the amount of substrate cleaved by the protease by measuring the optical density at 410 nm. The method was subjected to a validation procedure and deemed fit for its intended purpose.

Example 11. Quantitative Measurement of CIBENZA® DP100 Protease in Feed Samples from Customers The quantitative assay was performed on feed samples provided by a customer. The assay was as described in Example 10. The feed samples included a control diet feed sample lacking protease, and two feed samples containing CIBENZA® DP100 added at the recommended dosage. Protease activity in the control diet was below the limit of detection, while that in the diets containing CIBENZA® DP100 was 292 U/g and 279 U/g, which represent 97% and 93%, respectively, of the recommended dosage of protease activity.

The quantitative assay was also performed on feed samples provided by a different customer. The feed samples included four feed samples having CIBENZA® DP100, two of which were in the mash form and two of which had been pelleted. Protease activity in the two mash diets was 316 U/g and 321 U/g, while protease activity in the two pelleted diets was 263 U/g and 280 U/g. The protease activity measured in these samples represents 105%, 107%, 88%, and 93% of the recommended dosage of protease activity.

What is claimed is:

1. A method for detecting protease activity in a feed sample, the method comprising:
   (a) mixing the feed sample with a buffer comprising phosphate and about 0.01% to about 10% sodium dodecyl sulfate (SDS) to form a feed extract;
   (b) contacting an aliquot of the feed extract with a protease substrate to form a reaction mixture, wherein the protease substrate comprises a polypeptide attached to a chromophore;
   (c) incubating the reaction mixture under conditions such that proteolytic cleavage of the protease substrate leads to a color change in the reaction mixture; and
   (d) monitoring the color change in the reaction mixture, thereby detecting protease activity in the feed sample.

2. The method of claim 1, wherein the feed sample is a mash animal feed or pelleted animal feed.

3. The method of claim 1, wherein the protease is a protease derived from *Bacillus licheniformis*.

4. The method of claim 1, wherein the buffer at step (a) comprises about 50 mM to about 200 mM phosphate buffer at about pH 7 to about pH 11, and about 0.1% to about 5% SDS.

5. The method of claim 1, wherein the protease substrate is insoluble.

6. The method of claim 1, wherein the polypeptide of the protease substrate is casein, collagen, or gelatin and the chromophore of the protease substrate is an azurine dye.

7. The method of claim 1, wherein the buffer at step (a) comprises 100 mM sodium phosphate buffer at about pH 8 and 0.25% SDS.

8. The method of claim 1, wherein the feed sample is not ground prior to preparing the feed extract in step (a).

9. The method of claim 1, wherein the feed extract is filtered before contacting with the protease substrate at step (b).

10. The method of claim 1, wherein the reaction mixture at step (c) is incubated for about 15 min to about 90 min at about 50° C.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
```

```
-continued

<223> OTHER INFORMATION: SYNTHESIZED

<400> SEQUENCE: 1

Ala Ala Pro Phe
1

<210> SEQ ID NO 2
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 2

Ala Ala Pro Leu
1

<210> SEQ ID NO 3
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 3

Ala Ala Pro Arg
1

<210> SEQ ID NO 4
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 4

Ala Gly Ser Arg Gly Ala Gly Gln
1               5
```